US00PP23333P3

(12) United States Plant Patent
Scully et al.

(10) Patent No.: US PP23,333 P3
(45) Date of Patent: Jan. 15, 2013

(54) SEASHORE PASPALUM TURFGRASS NAMED 'ALOHA'

(50) Latin Name: *Paspalum vaginatum*
Varietal Denomination: Aloha

(75) Inventors: Brian T. Scully, Ft. Pierce, FL (US); Russell T. Nagata, Hilo, HI (US); Kevin E. Kenworthy, Gainesville, FL (US); Gregg S. Nuessly, Wellington, FL (US); Ronald H. Cherry, Loxahatchee, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 2293 days.

(21) Appl. No.: 11/188,229

(22) Filed: Jul. 25, 2005

(65) Prior Publication Data

US 2012/0198592 P1 Aug. 2, 2012

(51) Int. Cl.
*A01H 5/00* (2006.01)

(52) U.S. Cl. ..... Plt./384

(58) Field of Classification Search ..... Plt./388, Plt./387, 384
See application file for complete search history.

*Primary Examiner* — Susan McCormick Ewoldt
(74) *Attorney, Agent, or Firm* — Jondle & Associates, P.C.

(57) ABSTRACT

A newly discovered, and asexually propagated genotype of Seashore *Paspalum* turfgrass with a distinct set of agronomic, horticultural, morphological, and insect resistant traits.

5 Drawing Sheets

Genus and species name: This invention relates to a new and distinct genotype of Seashore *Paspalum* of the genus and species *Paspalum vaginatum* O. Swartz. It is described herein and designated as 'Aloha'.

BACKGROUND OF THE INVENTION

This invention was discovered and identified at the University of Hawaii's Lalamilo Research Farm in Kamuela. This research site is located on the north side of the island of Hawaii in the Kohala District at an elevation of 3,000 feet, which receives less than 20" of annual rainfall. It was selected in January 1999 as a seedling from the open pollination of a naturalized/local land race and coded as Breeding Line No. H99-47. It was initially selected as a 1.0 inch seedling, transferred to a small pot, and subsequently propagated asexually. It is one of a number of genotypes that were selected and/or collected in the region and initially screened for horticultural appearance. As H99-47 was advanced through the selection process, it was evaluated and compared to the standard commercial varieties for a number of traits presented herein, and ultimately received the proposed name 'Aloha'. Over a five year research and testing period in Florida 'Aloha' was propagated numerous times and has remained uniform and genetically consistent. The denomination of this new invention in 'Aloha'.

The distinctness of 'Aloha' from 'Sea Isle 1', 'Sea Dwarf' (SDX-1), and other Seashore *Paspalum* varieties is based on four sets of traits including; 1) floral morphology; 2) leaf and stolon morphology' 3) rate of growth and cover; and 4) insect resistance.

For the purpose of registration under the "International Convention for the Protection of New Varieties of Plants" (generally known by its French acronym UPOV Convention) and noting Sections 1612 of the Manual of Patent Examination Procedures this new variety of Seashore *Paspalum* of the present invention is named 'Aloha'.

BRIEF DESCRIPITION OF DRAWINGS

Figure 1:
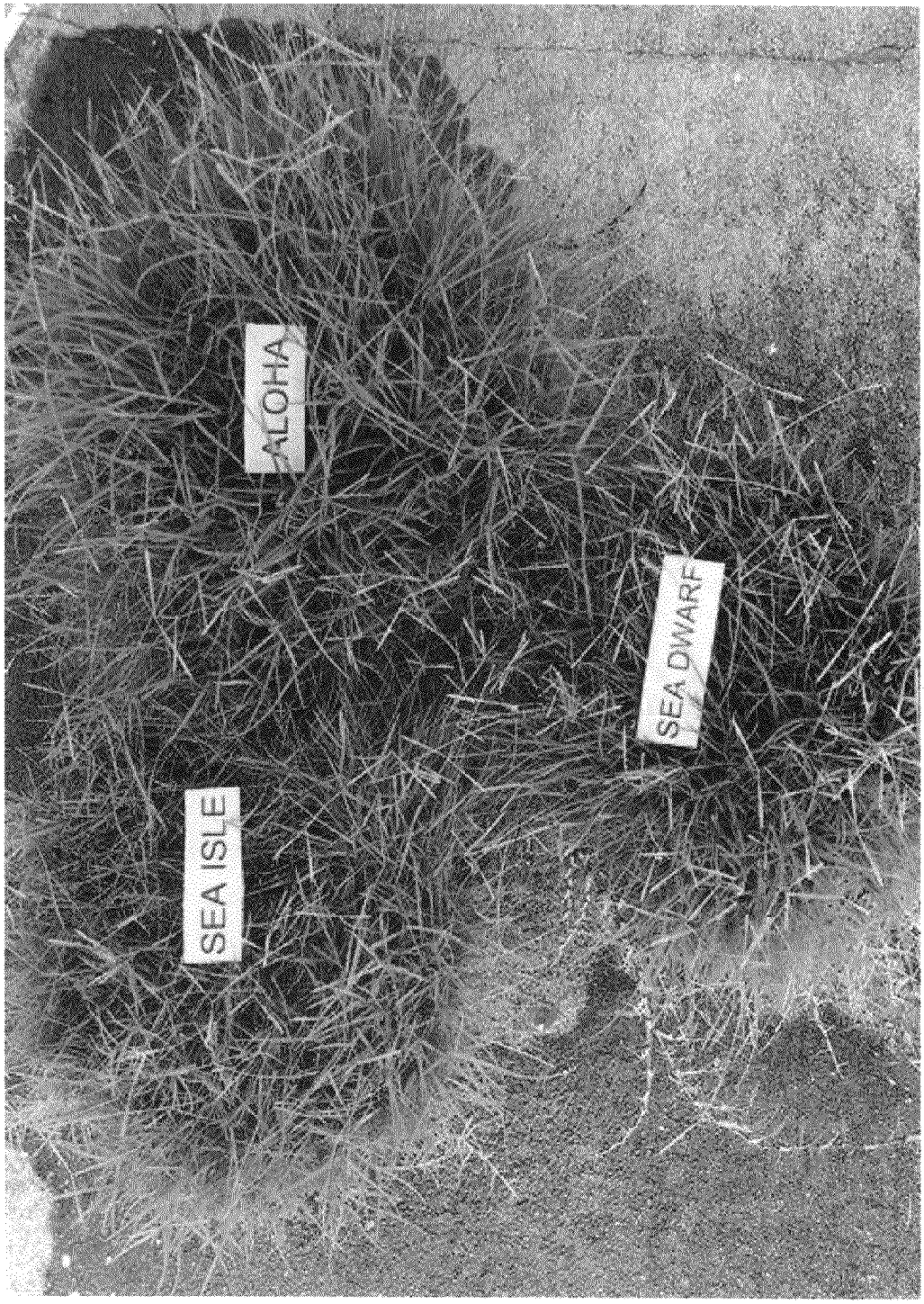

FIG. 1: A comparative "Aerial View" of 'Aloha', 'Sea Isle 1', and 'Sea Dwarf' (SDX-1) illustrating similarities in leaf morphology of 4 year-old plants. These pots were grown side-by-side, uncut and under identical cultural practices.

Figure 2:
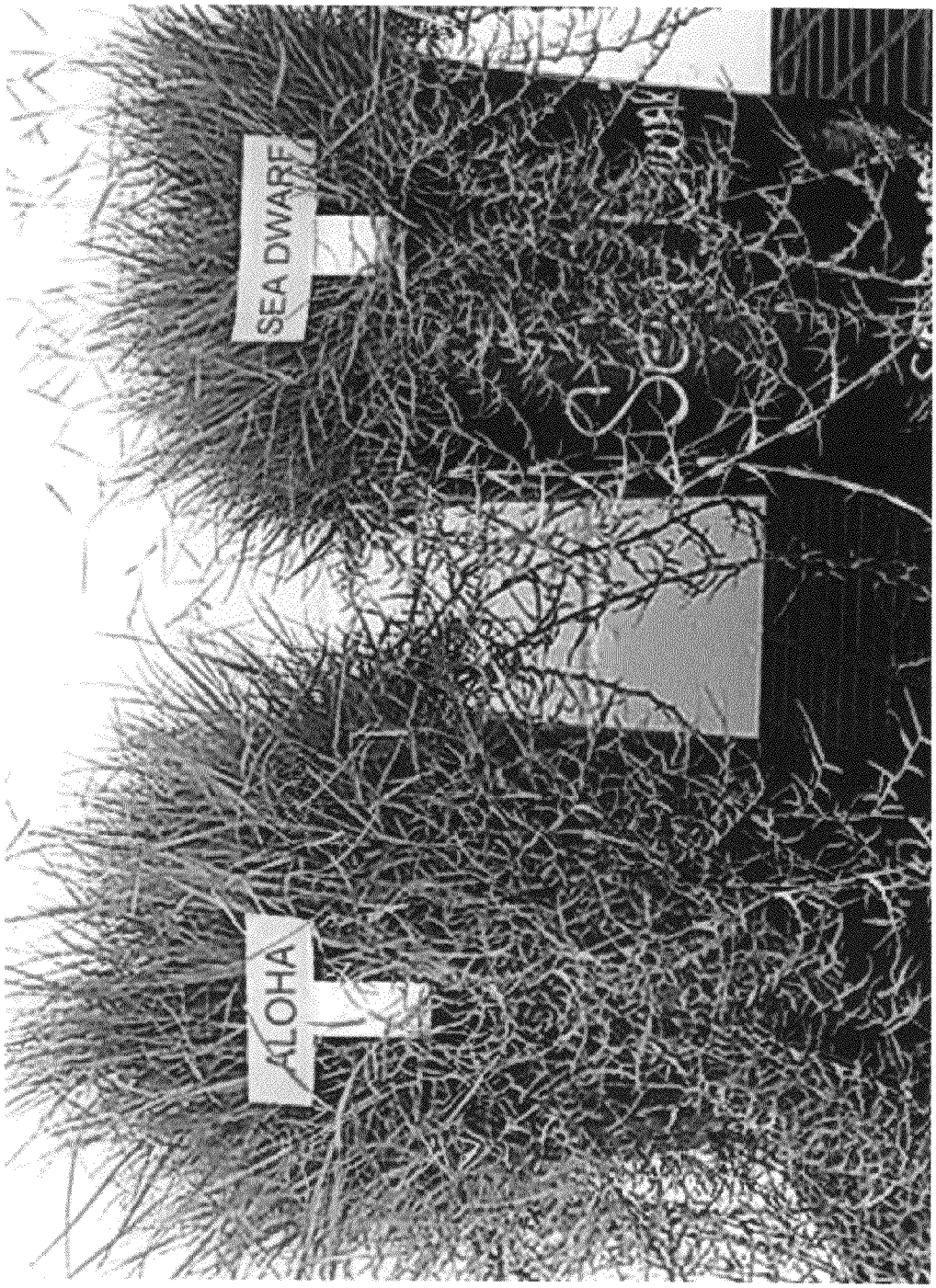

FIG. 2: A comparative photograph of 'Aloha' and 'Sea Dwarf' SDX-1) illustrating the differences in stolon morphology of 4 year-old plants. These pots were grown side-by-side, uncut and under identical cultural practices.

Figure 3:
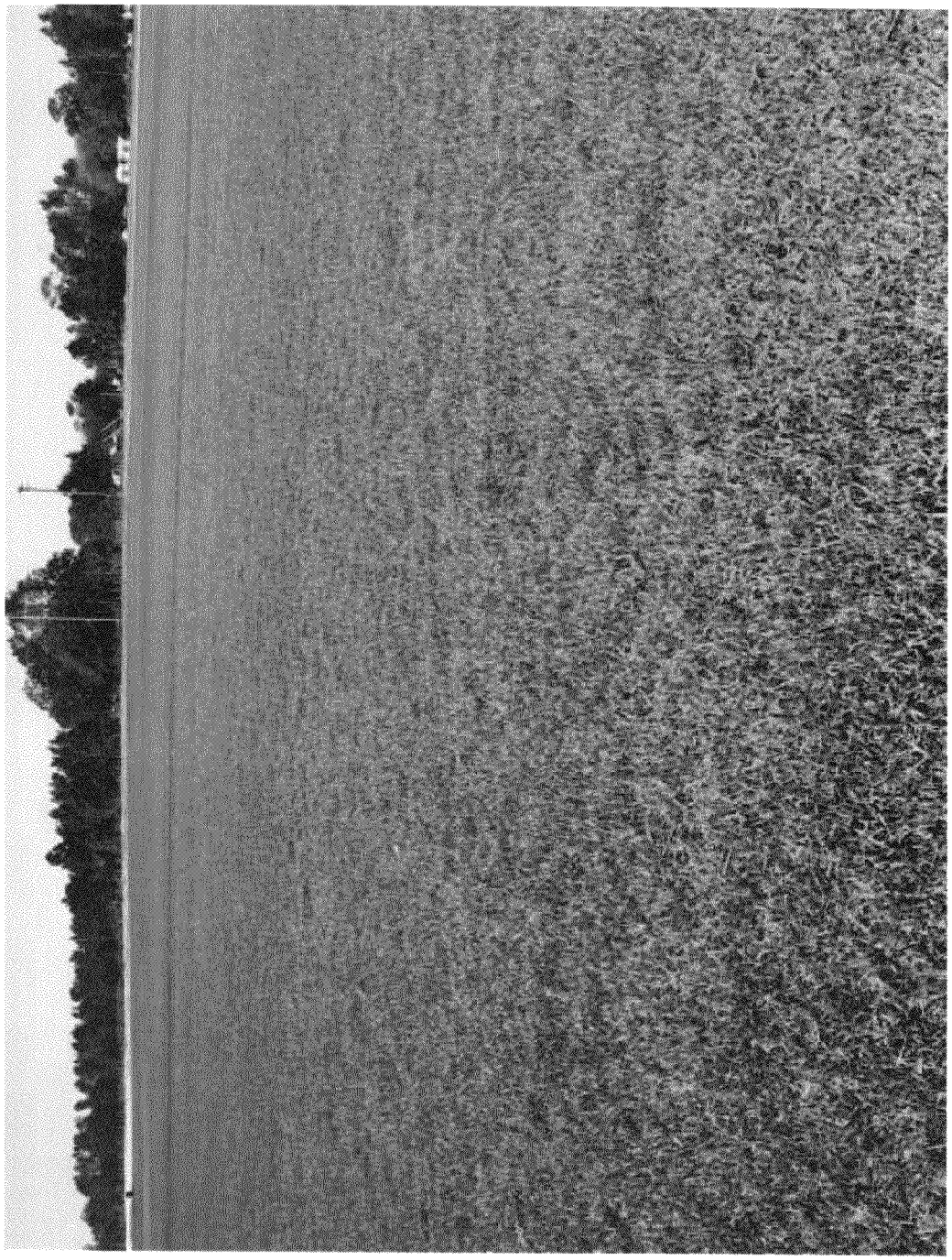

FIG. 3: A Breeders Block of 2 year-old 'Aloha' growing in Avon Park, Fla.

Figure 4:
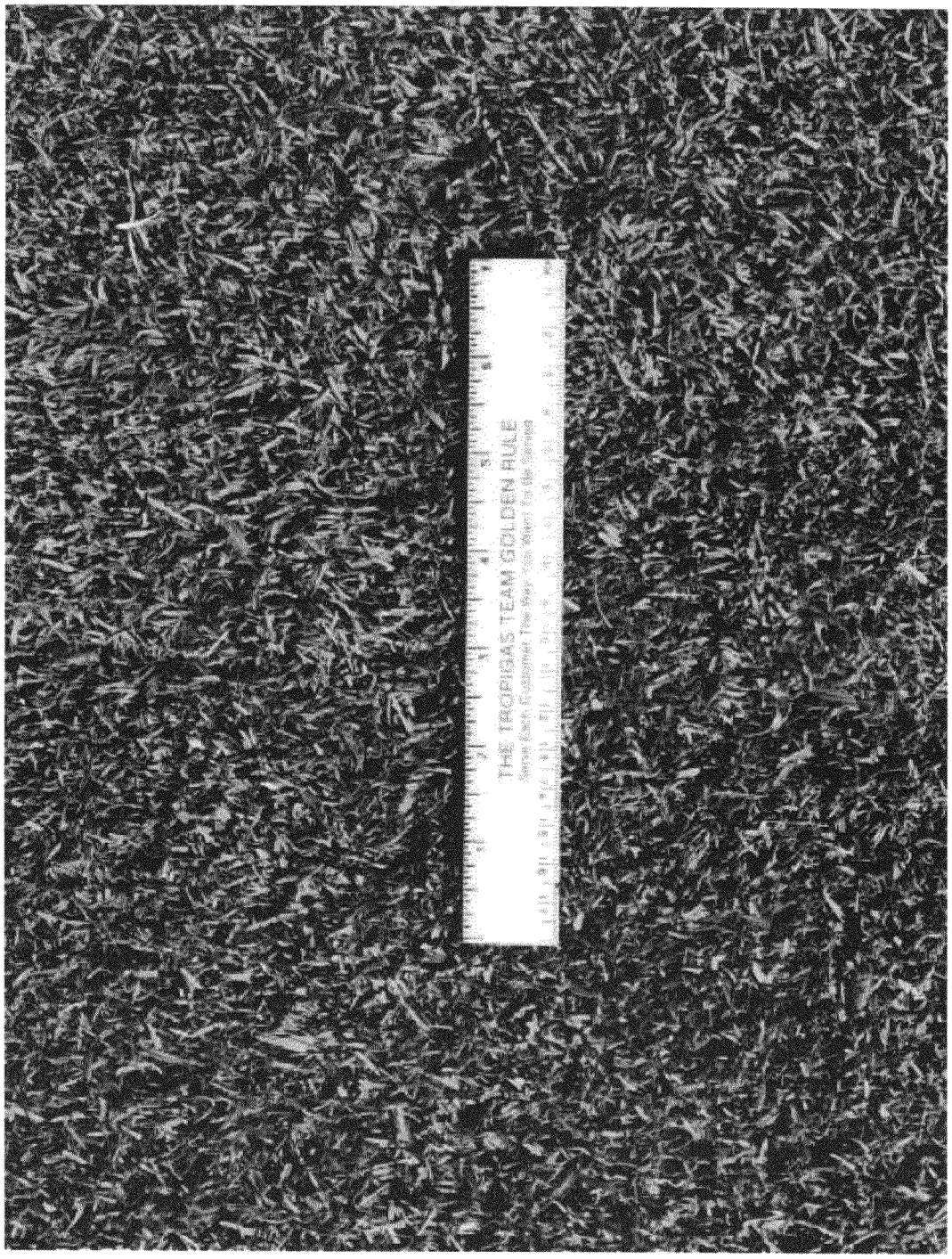

FIG. 4: A close-up photograph of a freshly cut Breeders Block of 2 year-old 'Aloha'.

Figure 5:
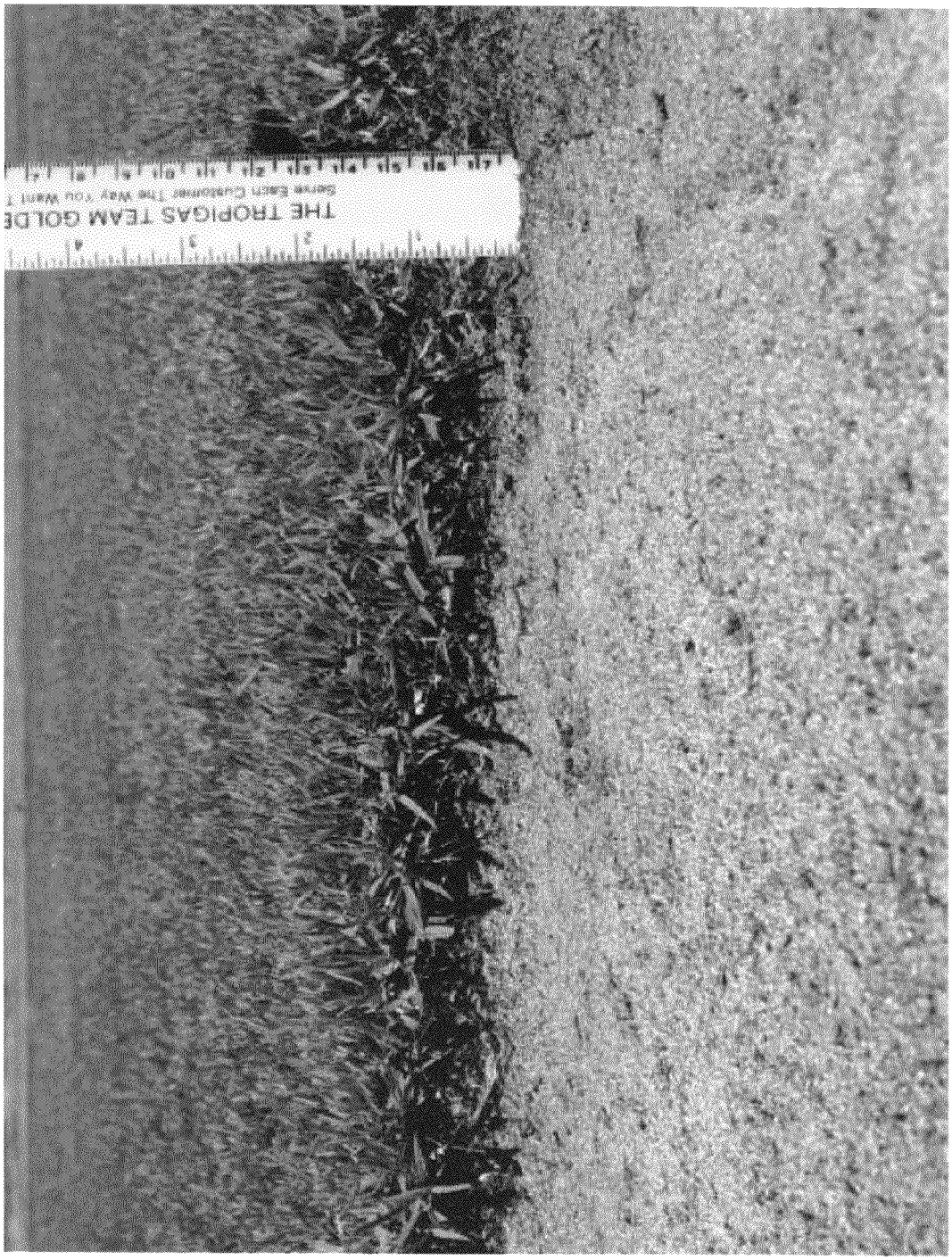

FIG. 5: A side profile photograph of 2 year-old 'Aloha' after a recent cutting.

DETAILED DESCRIPTION OF THE VARIETY

This new variety of Seashore *Paspalum* turfgrass is a perennial plant propagated asexually from either rhizomes, stolons, sprigs, or plugs. It is best adapted to tropical, subtropical, and sub temperate climates with moderate rainfall. 'Aloha' was tested under the code number H99-47 and is described under field conditions at three research sites in Florida, including Arcadia, Avon Park, and Belle Glade.

The floral morphology of 'Aloha' was compared to 'Sea Isle 1' and 'Sea Dwarf' across fourteen traits. Four of these traits described the peduncle morphology, and five were used to describe the racemes. Because *Paspalum vaginatum* has a bifurcated inflorescence, data were collected on both the long and short raceme (Table 1). Overall, 'Aloha' differed significantly from the standard varieties for eight of the fourteen-inflorescence traits. In general, 'Aloha' had a more robust floral morphology than either 'Sea Dwarf' or 'Sea Isle 1'. The total length of the inflorescence and the width of the peduncle were significantly longer for 'Aloha', while the exposed or exerted portion of the peduncle was shorter. As expected, the sheath of the flag leaf, which covers the peduncle was correspondingly longer on 'Aloha' (Table 2). Peduncle width on all three varieties varied less then 1.0 mm.

Raceme morphology varied both within and among the varieties. Within each variety, the long-racemes were 5.0% to 10.0% longer than the short-racemes, and the standard errors (s.e.) around the variety means indicated these differences were statistically significant for 'Aloha' and 'Sea Isle 1'. The differences between the long-and short-racemes on 'Sea Dwarf' were not significant. Among the varieties, 'Aloha' produced longer long-racemes and longer short-racemes than either of the standard varieties, and theses differences were statistically significant (Table 1). This pattern was repeated for floret number. Within varieties, there were more florets produced on the long-racemes as compared to the short-racemes, but only 'Sea Isle 1' exhibited a significant difference. Among the varieties, 'Aloha' produced more florets on both the long- and short-racemes than either of the standards (Table 1). Floret density across all varieties was the tightest on 'Sea Dwarf' and the least compact on 'Aloha'. Densities ranged from an average of one floret per 1.71 mm to 1.85 mm. For raceme width, glume length and glume width the pattern of size was either reversed or inconsistent. 'Sea Dwarf' had the widest racemes, and 'Aloha' had an intermediate raceme width (Table 1). 'Sea Dwarf' also had longer glumes than 'Aloha' on the short-racemes, but shorter glumes on the long-racemes (Table 1).

The morphology of the flag leaf is described by three traits, which include the flag leaf length and width, along with the sheath length. 'Aloha' had a more robust morphology then either 'Sea Isle 1' or 'Sea Dwarf' (Table 2). On average, the flag leaves of 'Aloha' were significantly longer and wider than either standard. 'Aloha' produced flag leaves that were 50% longer than 'Sea Dwarf' and nearly twice as long as the flag leaves produced by 'Sea Isle 1' (Table 2). In addition, the flag leaf sheaths covered more of peduncle on 'Aloha', and were significantly longer than the standards (Table 2).

The stolon and leaf morphology of the vegetative tissue was measured on fully expanded leaves and internodes. Unlike the previously measured traits, there were no significant differences between the three varieties for average leaf length or width. This is also illustrated in FIG. 1. From an uncut field plot, 'Aloha' produced leaves that were ±2.0 mm longer than 'Sea Dwarf' and ±4.5 mm longer than 'Sea Isle 1' 'Aloha' also produced leaves that were narrower (Table 3). Significant statistical differences did exist for the internode measurements. 'Aloha' and 'Sea Dwarf' had, on average, shorter internodes than 'Sea Isle 1' (Table 2). The internode width of 'Aloha' was significantly shorter than 'Sea Isle 1', but no significant difference was detected between 'Aloha' and Sea Dwarf for this trait (Table 3).

The green color and anthocyanin pigment in 'Aloha', 'Sea Dwarf' and 'Sea Isle 1' varied when fresh samples of vegetative tissue were compared to color panels in the Munsell Color Chart. The adaxial leaf surface of all three varieties ranged in the hue from 5GY to 7.5GY, but 'Aloha' [5GY-7.5GY (5-4/4)] had a darker color than either 'Sea Dwarf' [5GY (6-5/4) to 7.5GY (5-4/4)] or 'Sea Isle 1' [5GY-7.5GY (6-5/4)]. The green internode tissue of 'Aloha' ranged in color from [5GY (6-5/4) to 7.5GY (6-5/4)] and had a darker green color than either 'Sea Dwarf', [5GY (6-5/4) to 7.5GY (6-5/4)], or 'Sea Isle 1' [5GY (6-5/4) to 7.5GY (6-5/4)]. Anthocyanin colors in the node and internode tissues were essentially the same. Color patterns in the stigmatic tissue and racemes of each variety were also similar. The color of the exposed peduncle on 'Sea Dwarf' had more yellow [2.5GY (6-5/6)] than either 'Aloha' or 'Sea Isle 1', which had an identical color range of [5GY (6-5/6) to 7.5GY (6-5/6)].

A set of four varieties were compared for the rate of growth as measured by the increases in plot coverage, stolon count and stolon length. Stolon length was measured in centimeters. All four varieties in the "grow-in" experiments exhibited statistically significant differences from the first month of data collection. 'Aloha' covered the plots significantly faster than 'Sea Dwarf', 'Sea Green' or 'Sea Isle 1'. 'Aloha' attained 50% plot coverage in 3.75 months, while 'Sea Dwarf' took over eight months to attain 50% plot coverage. 'Sea Isle 1' and 'Sea Green' attained 50% plot coverage by the middle of the fifth month (Table 4). 'Aloha' and 'Sea Isle 1' produced the most stolons in the fourth month, but in subsequence months stolon numbers were difficult to discern as plot coverage increased. Across all months, 'Aloha' produced more stolons than any of the standard varieties (Table 4). The measurements of stolon length indicated that only 'Sea Dwarf' produced consistently shorter stolons than either 'Aloha', 'Sea Green' or 'Sea Isle 1'.

'Aloha' was compared to an array of varieties for resistance to the greenbug aphid (*Schizaphes graminum* (Rondani) (Homoptera: Aphidae) and the tropical sod webworm (*Herpetogramma phaeoteralis* Guenee (Hepidoptera: Pyralidae). Both insects are known to attack and damage turfgrass, although the greenbug aphid is a relatively new problem on Seashore *Paspalum*. Five varieties of Seashore *Paspalum* were infested with two nymph colonies of the greenbug aphid, which were monitored for their rate of development, longevity and fecundity (Table 5). Aphids grown on 'Aloha' and 'Sea Isle 1' took the longest time to reach sexual maturity, and this development rate was significantly different from 'Sea Dwarf' and 'Sea Way'. The life expectancy or longevity of the aphids was significantly shorter on 'Aloha' than any of the other varieties. The aphids only lived for an average of 16.3 days on 'Aloha', while the life expectancy ranged from 24.9 to 29.4 days on the other varieties (Table 5). Additionally, the reproductive rate of the aphid was significantly reduced on 'Aloha' in comparison to the other varieties. Sexually mature aphids only produced an average of 14.6 offspring on 'Aloha', but an average of 29.1 to 38.4 offspring were produced on the four other varieties (Table 5). These results clearly indicate that 'Aloha' has a higher level of host plant resistance based on antibiosis in comparison to the other varieties.

In a second set of experiments, 'Aloha' was compared to the same standard varieties and 'Sea Wolf', a pasture-type Seashore *Paspalum*, for the growth of the tropical sod webworm. No statistically significant differences existed between the turf varieties of Seashore *Paspalum*, although 'Aloha' induced the lowest insect weight gain among this group of varieties. 'Sea Wolf' was the only variety to significantly slow the rate of webworm weight gain among all varieties (Table 6).

TABLE 1

Comparison of floral traits among 'Aloha', 'Sea Isle 1', and 'Sea Dwarf' (SDX-1).

| | 'Aloha' | | 'Sea Isle' | | 'Sea Dwarf' | |
|---|---|---|---|---|---|---|
| Trait | Mean | ± | Mean | ± | Mean | ± |
| Overall Shoot [Z] | 94.70 | 1.66 | 84.05 | 1.56 | 82.01 | 1.87 |
| Peduncle [Y] | 61.03 | 1.34 | 54.56 | 1.28 | 52.93 | 1.54 |
| Peduncle Width [X] | 0.98 | 0.02 | 0.90 | 0.02 | 0.98 | 0.04 |
| Exposed [W] | 12.24 | 0.82 | 12.87 | 1.00 | 13.77 | 0.79 |
| Long Raceme | | | | | | |
| Raceme [V] | 34.30 | 0.50 | 29.20 | 0.46 | 28.60 | 0.86 |
| Raceme Width [U] | 1.54 | 0.03 | 1.42 | 0.02 | 1.69 | 0.03 |
| Floret [T] | 18.25 | 0.48 | 16.50 | 0.36 | 16.70 | 0.54 |
| Glume Length [S] | 3.10 | 0.02 | 3.02 | 0.02 | 2.92 | 0.05 |
| Glume Width [R] | 1.51 | 0.03 | 1.48 | 0.01 | 1.38 | 0.03 |
| Short Raceme | | | | | | |
| Raceme [V] | 31.75 | 0.51 | 26.38 | 0.57 | 26.38 | 0.77 |
| Raceme Width [U] | 1.70 | 0.05 | 1.59 | 0.05 | 1.77 | 0.05 |
| Floret [T] | 17.40 | 0.50 | 14.50 | 0.44 | 14.95 | 0.65 |
| Glume Length [S] | 2.75 | 0.06 | 2.76 | 0.04 | 2.86 | 0.04 |
| Glume Width [R] | 1.17 | 0.02 | 1.18 | 0.03 | 1.13 | 0.03 |

[Z] Overall Shoot Length (mm) is measured from the first node on the peduncle subtending the inflorescence to the top of the longest raceme.
[Y] Peduncle Length (mm) is measured from first node subtending the inflorescences to the point where the bifurcation is initiated.
[X] Peduncle Width (mm) is measured at the widest part of the peduncle.
[W] Exposed Peduncle Length (mm) is the average length of the peduncle not covered by the flag leaf sheath.
[V] Raceme Length (mm) is measured from the apex of each seed head to the base of the raceme.
[U] Raceme Width (mm) is measured at the broadest part of each seed head.
[T] Floret Number is the average count of seed producing florets on the raceme.
[S] Glume Length (mm) is a measure of the average glume length on the seed located at the mid-point along the floret.
[R] Glume Width (mm) is measured at the widest part of the glume.

TABLE 2

Comparison of Flag Leaf traits among 'Aloha', 'Sea Isle 1', and 'Sea Dwarf' (SDX-1)

| | 'Aloha' | | 'Sea Isle' | | 'Sea Dwarf' | |
|---|---|---|---|---|---|---|
| Trait (mm) | Mean | ± | Mean | ± | Mean | ± |
| Flag Leaf Length | 7.64 | 0.88 | 3.85 | 0.64 | 4.53 | 0.79 |
| Flag Leaf Width [Z] | 1.01 | 0.09 | 0.61 | 0.09 | 0.66 | 0.11 |
| Sheath Length [Y] | 48.82 | 0.87 | 41.42 | 0.88 | 39.89 | 0.82 |

[Z] Flag Leaf Width is measured at the widest part of the leaf.
[Y] Sheath Length is measured from the base of the flag leaf to the first node subtending the inflorescence.

TABLE 3

Comparison of Leaf morphology among 'Aloha', 'Sea Isle 1', and 'Sea Dwarf' (SDX-1)

| | 'Aloha' | | 'Sea Isle' | | 'Sea Dwarf' | |
|---|---|---|---|---|---|---|
| Trait (mm) | Mean | ± | Mean | ± | Mean | ± |
| Leaf Length | 58.90 | 1.38 | 54.36 | 1.80 | 57.95 | 2.18 |
| Leaf Width [Z] | 2.94 | 0.07 | 3.05 | 0.09 | 3.03 | 0.10 |
| Internode Length | 24.07 | 0.76 | 27.21 | 0.73 | 22.28 | 0.85 |
| Internode Width [Y] | 1.76 | 0.04 | 1.90 | 0.03 | 1.83 | 0.03 |

[Z] Flag Leaf Width is measured at the widest part of the leaf.
[Y] Internode Width is measured at the widest part of the internode

TABLE 4

A comparison of 'Aloha', 'Sea Dwarf', 'Sea Green', and 'Sea Isle 1' for rate of plot cover, stolon count and stolon length.

| Trait | Month 1 | | Month 2 | | Month 3 | | Month 4 | |
|---|---|---|---|---|---|---|---|---|
| Variety | Mean | ± s.e. | Mean | ± s.e. | Mean | ± s.e. | Mean | ± s.e. |
| % Cover [Z] | | | | | | | | |
| 'Aloha' | 8.75 | 0.25 | 25.75 | 3.20 | — | — | 55.50 | 7.71 |
| 'Sea Dwarf' | 9.00 | 0.41 | 14.74 | 2.06 | — | — | 31.25 | 1.75 |
| 'Sea Green' | 7.00 | 2.27 | 23.00 | 6.50 | — | — | 43.25 | 1.94 |
| 'Sea Isle | 9.50 | 1.50 | 29.25 | 4.11 | — | — | 47.50 | 2.50 |
| Stolon Count [Y] | | | | | | | | |
| 'Aloha' | 18.00 | 1.91 | 40.30 | 1.19 | — | — | 41.25 | 4.64 |
| 'Sea Dwarf' | 16.25 | 1.44 | 39.00 | 1.91 | — | — | 33.75 | 5.49 |
| 'Sea Green' | 11.75 | 1.75 | 35.00 | 2.83 | — | — | 36.00 | 4.04 |
| 'Sea Isle | 17.75 | 2.66 | 35.75 | 3.68 | — | — | 42.25 | 1.31 |
| Stolon Length [X] | | | | | | | | |
| 'Aloha' | 8.29 | 0.48 | 19.00 | 0.58 | — | — | 21.50 | 1.50 |
| 'Sea Dwarf' | 4.50 | 0.50 | 13.50 | 0.90 | — | — | 15.25 | 1.25 |
| 'Sea Green' | 6.00 | 1.22 | 19.00 | 1.29 | — | — | 20.50 | 2.25 |
| 'Sea Isle | 7.75 | 1.31 | 19.50 | 0.50 | — | — | 20.25 | 2.72 |

| Trait | Month 5 | | Month 6 | | Month 7 | | Month 8 | |
|---|---|---|---|---|---|---|---|---|
| Variety | Mean | ± s.e. | Mean | ± s.e. | Mean | ± s.e. | Mean | ± s.e. |
| % Cover [Z] | | | | | | | | |
| 'Aloha' | — | — | 71.25 | 8.98 | — | — | 68.75 | 11.06 |
| 'Sea Dwarf' | — | — | 40.00 | 6.12 | — | — | 43.75 | 8.00 |
| 'Sea Green' | — | — | 52.50 | 4.33 | — | — | 57.50 | 3.23 |
| 'Sea Isle | — | — | 56.25 | 1.25 | — | — | 56.25 | 4.27 |
| Stolon Count [Y] | | | | | | | | |
| 'Aloha' | — | — | 23.00 | 1.47 | — | — | 23.00 | 1.47 |
| 'Sea Dwarf' | — | — | 17.75 | 0.63 | — | — | 19.00 | 0.71 |
| 'Sea Green' | — | — | 22.00 | 1.91 | — | — | 22.25 | 1.80 |
| 'Sea Isle | — | — | 21.75 | 0.75 | — | — | 22.00 | 0.71 |
| Stolon Length [X] | | | | | | | | |
| 'Aloha' | — | — | 27.00 | 2.12 | — | — | 28.75 | 2.63 |
| 'Sea Dwarf' | — | — | 20.50 | 2.53 | — | — | 23.00 | 2.65 |
| 'Sea Green' | — | — | 28.50 | 0.50 | — | — | 31.50 | 1.71 |
| 'Sea Isle | — | — | 26.00 | 2.45 | — | — | 29.50 | 2.06 |

[Z] Percent Cover is measured as the portion of the 1.0 $m^2$ plot covered in a particular month.
[Y] Stolon Number is the count of stolons radiating from a single 10 cm plug planted at the center of 1.0 $m^2$ plot.
[X] Stolon Length is the average length of stolons counted in a particular month. Stolon length is measured in cm.

TABLE 5

The Rate of Development, Longevity, and Fecundity of the green bug (*Schizaphis graminum*) feeding on five different varieties of Seashore Paspalum.

| | Development [Z] | | Longevity [Y] | | Fecundity [X] | |
|---|---|---|---|---|---|---|
| Variety | Mean | ± | Mean | ± | Mean | ± |
| 'Aloha' | 8.20 | 0.10 | 16.30 | 1.70 | 14.60 | 2.70 |
| 'Sea Isle' | 8.20 | 0.20 | 24.90 | 2.20 | 29.10 | 3.80 |
| 'Sea Dwarf' | 7.60 | 0.20 | 26.10 | 2.80 | 38.30 | 3.70 |
| 'Sea Green' | 7.90 | 0.20 | 26.60 | 3.40 | 34.00 | 4.10 |
| 'Sea Way' | 7.60 | 0.30 | 29.40 | 3.00 | 38.40 | 6.00 |

[Z] The Rate of Development is defined as the number of days to reproductive maturity.
[Y] Longevity is the average life expectancy measured in days.
[X] Fecundity is a measure of the reproductive rate and based on offspring count.

TABLE 6

Weight gain for the tropical sod webworm (*Herpetogramma phaeopterali* Guemee) after four days of feeding on six different varieties of Seashore Paspalum.

| | Weight [Z] | | Range | |
|---|---|---|---|---|
| Variety | Mean | ± | Mean | ± |
| 'Aloha' | 50.90 | 4.76 | 24.10 | 68.70 |
| 'Sea Isle 1' | 56.27 | 2.76 | 43.20 | 73.80 |
| 'Sea Dwarf' | 51.14 | 3.86 | 29.50 | 70.60 |
| 'Sea Green' | 58.38 | 5.33 | 24.40 | 78.80 |

TABLE 6-continued

Weight gain for the tropical sod webworm (*Herpetogramma phaeopterali* Guemee) after four days of feeding on six different varieties of Seashore Paspalum.

| | Weight [Z] | | Range | |
|---|---|---|---|---|
| Variety | Mean | ± | Mean | ± |
| 'Sea Way' | 51.61 | 3.81 | 32.70 | 70.00 |
| 'Sea Wolf' | 30.43 | 4.47 | 12.50 | 55.10 |

[Z] Weight gain is measured in mg.

We claim:

1. A new and distinct genotype of Seashore *Paspalum* turfgrass plant substantially described and illustrated herein.

* * * * *